(12) United States Patent
Han et al.

(10) Patent No.: US 11,540,736 B2
(45) Date of Patent: Jan. 3, 2023

(54) WEARABLE ELECTRONIC DEVICE INCLUDING BIOMETRIC SENSOR

(71) Applicant: Samsung Electronics Co., Ltd., Gyeonggi-do (KR)

(72) Inventors: Seonho Han, Gyeonggi-do (KR); Taegyun Kim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 389 days.

(21) Appl. No.: 16/788,343

(22) Filed: Feb. 12, 2020

(65) Prior Publication Data
US 2020/0260972 A1    Aug. 20, 2020

(30) Foreign Application Priority Data

Feb. 18, 2019    (KR) ........................ 10-2019-0018842

(51) Int. Cl.
*A61B 5/024*         (2006.01)
*G06F 1/16*          (2006.01)
(Continued)

(52) U.S. Cl.
CPC ........ *A61B 5/02427* (2013.01); *A61B 5/0261* (2013.01); *G06F 1/163* (2013.01); (Continued)

(58) Field of Classification Search
CPC . A61B 5/02427; A61B 5/0261; A61B 5/6803; A61B 5/681; A61B 2560/0456;
(Continued)

(56) References Cited

U.S. PATENT DOCUMENTS

| 2015/0201854 A1 | 7/2015 | Hong et al. |
| 2017/0000350 A1* | 1/2017 | Kwon ................... A61B 5/021 |

(Continued)

FOREIGN PATENT DOCUMENTS

| JP | 11-014453 A | 1/1999 |
| JP | 2016-053492 A | 4/2016 |
| KR | 10-2018-0042472 A | 4/2018 |

OTHER PUBLICATIONS

International Search Report dated May 28, 2020.
European Search Report dated Oct. 29, 2020.

*Primary Examiner* — Jason M Sims
*Assistant Examiner* — Abid A Mustansir
(74) *Attorney, Agent, or Firm* — Cha & Reiter, LLC

(57) ABSTRACT

A wearable electronic device is disclosed, including: a housing having a front plate disposed facing in a first direction, a rear plate disposed facing in a second direction opposite to the first direction, at least a part of the rear plate substantially transparent, and a side member defining a space between the front plate and the rear plate, a substrate disposed within the space, a biometric sensor module disposed between the substrate and the rear plate including at least one light source configured to emit light to an exterior of the wearable electronic device and at least one light detector configured to receive reflected light corresponding to the emitted light reflected from the exterior, and at least one magnetic substance disposed between the light source and the light detector to limit an amount of light reaching the biometric sensor module other than the reflected emitted light.

19 Claims, 8 Drawing Sheets

(51) Int. Cl.
    *A61B 5/026*     (2006.01)
    *A61B 5/00*     (2006.01)

(52) U.S. Cl.
    CPC ............ *A61B 5/681* (2013.01); *A61B 5/6803* (2013.01); *A61B 2560/0456* (2013.01); *A61B 2562/185* (2013.01)

(58) Field of Classification Search
    CPC ...... A61B 2562/185; A61B 2560/0214; A61B 2560/0406; A61B 2562/166; A61B 5/02416; A61B 5/02438; A61B 5/0059; G06F 1/163; G06F 1/1684; H01F 7/0247; H02J 50/10; H02J 50/90
    See application file for complete search history.

(56) References Cited

U.S. PATENT DOCUMENTS

| | | | |
|---|---|---|---|
| 2017/0011210 A1* | 1/2017 | Cheong | A61B 5/681 |
| 2017/0209055 A1* | 7/2017 | Pantelopoulos | A61B 5/7203 |
| 2017/0315511 A1* | 11/2017 | Shim | A61B 5/7221 |
| 2018/0116532 A1 | 5/2018 | Han et al. | |
| 2018/0175643 A1 | 6/2018 | Shim et al. | |

\* cited by examiner

WEARABLE ELECTRONIC DEVICE INCLUDING BIOMETRIC SENSOR

CROSS-REFERENCE TO RELATED APPLICATION(S)

This application is based on and claims priority under 35 U.S.C. 119 to Korean Patent Application No. 10-2019-0018842, filed on Feb. 18, 2019, in the Korean Intellectual Property Office, the disclosure of which is herein incorporated by reference in its entirety.

TECHNICAL FIELD

Certain embodiments relate to a wearable electronic device having a sensor capable of acquiring, based on optics, biometric information.

BACKGROUND

Modern day electronic devices include home appliances and devices that perform specific functions according to programs installed therein, such as electronic diaries, portable multimedia players, mobile communication terminals, tablet PCs, video/audio devices, desktop/laptop computers, navigation systems for vehicles, etc.

For example, these electronic devices may output stored information in the form of multimedia including sound and/or imagery. With the increased integration of electronic devices and the popularization of hyper-speed and high-capacity wireless communications, a single mobile communication terminal has increased in sophistication as to be able to implement various functions. For example, a single device may integrate the ability to execute an entertainment function, such as a game, a multimedia function, such as reproducing music/video files, a communication and security function for mobile banking, a scheduling function, an electronic wallet function, etc., beyond the traditional role of executing a communication function.

Wearable electronic devices have been developed including various shapes and for factors (for example, "smart" eye-glasses or wrist-watches), such that the electronic devices can be utilized while worn on human bodies. Whereas previously, it was sufficient for these wearable electronic devices to perform one or two functions, but recent trends indicate a market desire that implementation of a greater diversity of functions in wearable electronic devices, as in the case of mobile communication terminals.

SUMMARY

Because of the compact size of most wearable electronic devices, mounting space for components is usually very limited. Accordingly, it is imperative to dispose the components of the device in optimized locations to improve the efficiency of utilization of the available space.

For example, when mounting a sensor capable of acquiring biometric information on a wearable electronic device, ensuring reliability of the sensor through accurate calibration may be crucial. In the case of a photoplethysmography (PPG) sensor, which acquires biometric information based on optics, it may be beneficial to prevent light leakage inside the electronic device, and to reduce direct exposure of the sensor to sunlight to minimize environmental noise, and thereby enable sampling at a sufficient luminance.

According to an embodiment, various components such as a biometric sensor module, a battery charging module, and a magnetic substance may be mounted adjacent to the rear plate of a wearable electronic device. It is desirable in this regard to consider the optimized position of each component such that the components can fully exhibit their functions, and the position of a specific component in which the same can fully exhibit its function may limit the design of another component.

Certain embodiments may provide a wearable electronic device including a biometric sensor based on optics, the electronic device having improved component mounting characteristics and increased design degree-of-freedom.

According to certain embodiments, there may be provided a wearable electronic device including: a housing comprising a front plate disposed facing in a first direction, a rear plate disposed facing in a second direction opposite to the first direction, at least a part of the rear plate substantially transparent, and a side member coupled to the front and rear plates to define a space between the front plate and the rear plate, a substrate disposed within the space, a biometric sensor module disposed between the substrate and the rear plate, the biometric sensor module including at least one light source configured to emit light to an exterior of the wearable electronic device and at least one light detector configured to receive reflected light corresponding to the emitted light reflected from the exterior, and at least one magnetic substance disposed between the light source and the light detector to limit an amount of light reaching the biometric sensor module other than the reflected emitted light.

According to certain embodiments, there may be provided a wearable electronic device including: a housing comprising a front plate disposed facing in a first direction, a rear plate disposed facing in a second direction opposite to the first direction, at least a part of the rear plate being substantially transparent, and a side member coupled to the front and rear plates to define a space between the front plate and the rear plate, a substrate disposed within the space, an optical biometric sensor module disposed between the substrate and the rear plate, the optical biometric sensor module, including an optical biometric sensor driver, at least one light source configured to emit light to an exterior of the wearable electronic device, at least one light detector configured to receive the emitted light reflected from the exterior, a bracket on which the optical biometric sensor driver, the light source, and the light detector are seated, a circuit structure extending from one side of the substrate, an optical biometric sensor connector formed on an end of the circuit structure, a wireless charging module configured to wirelessly charge the wearable electronic device, at least one magnetic substance configured to be arranged between the light source and the light detector, a member configured to forming a stacking structure with the magnetic substance, wherein the wireless charging module is disposed so as to circumferentially surround at least a part of the optical biometric sensor module, and wherein the magnetic substance includes a wall formed thereon to limit an incident of light reaching the light detector other than the reflected emitted light.

Certain embodiments may provide a shield structure efficiently preventing light emitted by a light source from leaking from a designated light path along which the light is incident onto a light detector to another path.

According to an embodiment, a magnetic substance for enabling attachment/detachment during wireless charging may be used as the shield structure. By arranging the shield structure having magneticity between the light source and the light detector, it is possible to avoid limitations on the design and the component mounting characteristics of other components inside the device, including a coil portion.

BRIEF DESCRIPTION OF THE DRAWINGS

The above and other aspects, features, and advantages of the disclosure will be more apparent from the following detailed description taken in conjunction with the accompanying drawings, in which.

DETAILED DESCRIPTION

Figure 1:
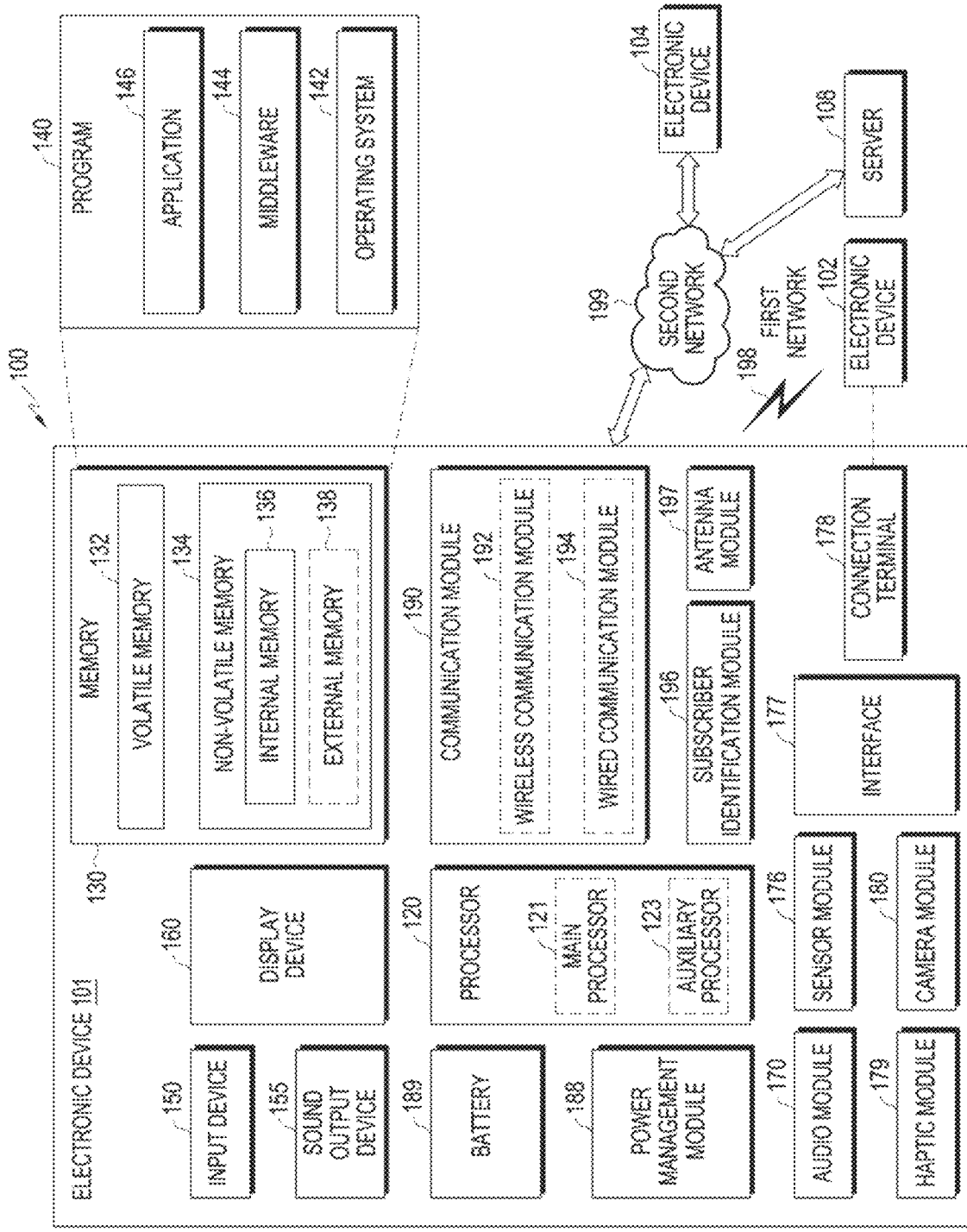
FIG. 1 is block diagram of an electronic device inside a network environment according to certain embodiments.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing recordings, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his or her tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element implemented by a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figures 2A, 2B:
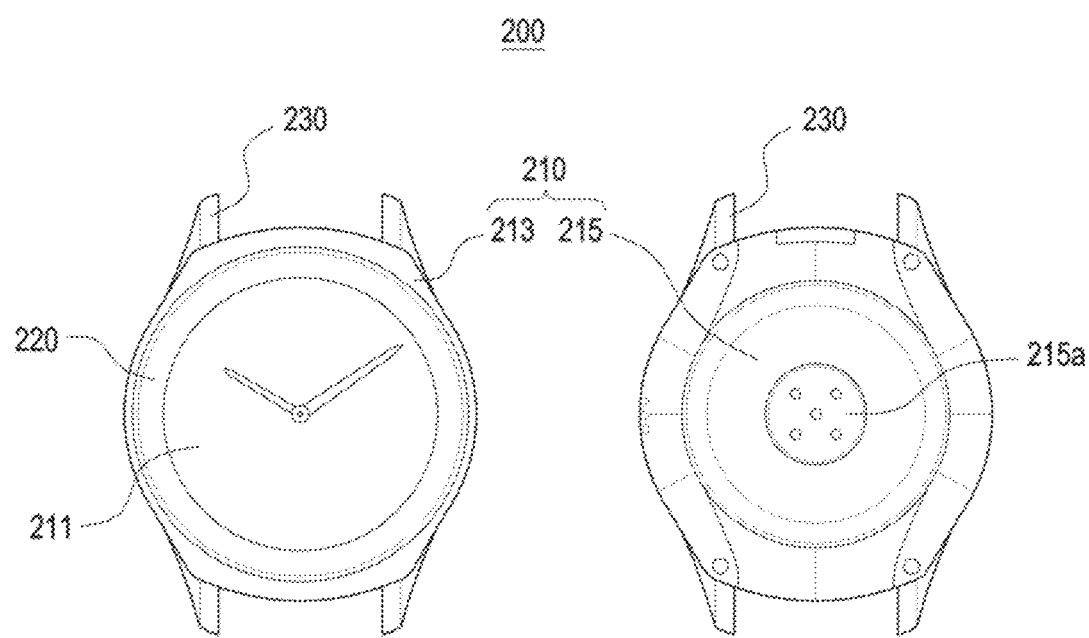
FIG. 2A is a diagram illustrating an electronic device according to one of certain embodiments.
FIG. 2B is a diagram illustrating an electronic device according to one of certain embodiments.

FIG. 2A is a diagram illustrating an example electronic device according to one of certain embodiments, and FIG. 2B is a diagram illustrating an example electronic device according to one of certain embodiments. More specifically, FIG. 2A is a front view of the example electronic device, and FIG. 2B is a rear view of the example electronic device seen in a different direction.

An electronic device according to certain embodiments may be a portable electronic device such as a mobile communication terminal, or a wearable electronic device that can be worn on a user's body. A smartwatch will be described as an example of the electronic device according to certain embodiments.

Referring to FIG. 2A and FIG. 2B, the electronic device 200 according to certain embodiments may include a housing 210 including a transparent plate 211, a bezel 220, and attachment/detachment portions 230. As used herein to describe certain embodiments, "first direction" may refer to a direction perpendicular to a surface of the transparent plate 211, and "second direction" may refer to the opposite direction of the first direction.

According to certain embodiments, the housing 210 may include a first surface 213 facing the first direction and a second surface 215 facing in the second direction that is opposite to the first direction. The front surface of the housing 210 may be open, and the transparent plate 211 may be mounted so as to form at least a part of the first surface 213, which corresponds to the front surface of the housing 210, thereby covering the open first surface 213 of the housing 210. Each of the first surface 213 and the second surface 215 may have a plate shape and may include a curved surface on the periphery part thereof. The second surface 215 of the housing 210 may include at least one transparent area 215a such that light generated by an optical element (for example, light source) disposed within the housing may be emitted outwards.

According to certain embodiments, various kinds of circuit devices, such as the processor 120 (for example, application processor (AP)), the memory 130, the input/output interface 150, and the communication interface 190, which have been described above with reference to FIG. 1, may be contained inside the housing 210, and a battery (not illustrated) may also be contained therein so as to secure power supply.

According to certain embodiments, the housing 210 may be made of a metal material. According to certain embodiments, a part (for example, edge) of the housing 210 may be made of a metal material, and another part of the housing 210 may be made of a plastic material.

According to certain embodiments, the transparent plate 211 may be arranged on the first surface 213 of the housing 210. The transparent plate 211 may be made of a transparent material, for example, glass or resin (for example, acrylic resin or polycarbonate), so as to implement a screen output from the display device (for example, 160 in FIG. 1). For example, an analog watch-type screen may be output to the transparent plate 211.

According to certain embodiments, the bezel 220 may be arranged on the edge of the transparent plate 211. The bezel 220 may be coupled to be able to rotate relative to the housing 210 such that the bezel 220 rotates along the edge of the transparent plate 211. The bezel 220 may be made of a metal material to give the electronic device 200 an aesthetic appearance. According to an embodiment, the bezel 220, when made of a metal material, may be used as an antenna radiator.

According to certain embodiments, the attachment/detachment portions 230 may be arranged to extend and to protrude away from both ends of the housing 210, respectively. The attachment/detachment portions 230 may be coupled to wearing portions (not illustrated) arranged to be worn on the user's wrist. The attachment/detachment portions 230 may have clamping grooves formed thereon so as to engage with the wearing portions. Multiple clamping grooves may be formed on the side surface of the housing 210, or may have the shape of closed curves extending along the periphery of the housing 210. The wearing portions may be configured in various types (for example, rubber material, plastic, metal, or the like), and the various kinds of wearing portions may be attached to/detached from the attachment/detachment portions 230 of the electronic device 200 according to the user's preferences, thereby giving the electronic device an aesthetic appearance.

Figure 3:
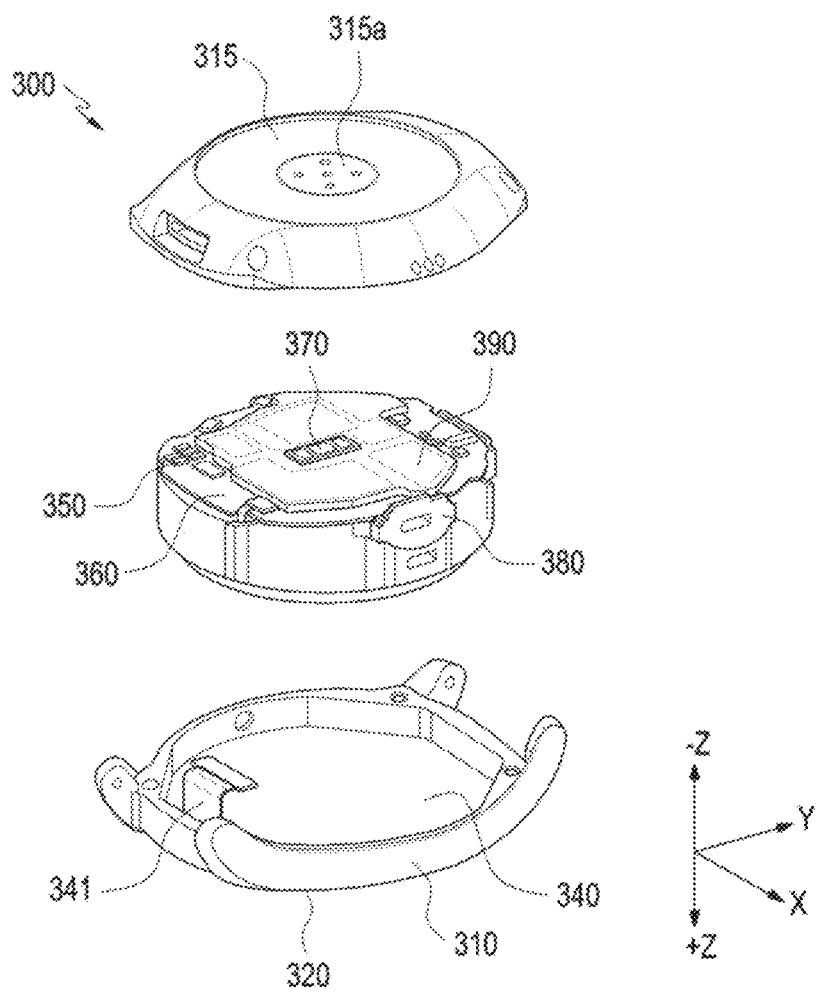
FIG. 3 is an exploded perspective view illustrating the inner structure of an electronic device according to one of certain embodiments.

FIG. 3 is an exploded perspective view illustrating the inner structure of an example electronic device according to one of certain embodiments.

In FIG. 3, "X" of the three-axis rectangular coordinate system may refer to the width-wise direction of the electronic device 300, "Y" may refer to the longitudinal (e.g., length-wise) direction of the electronic device 300, and "Z" may refer to the thickness (e.g. height-wise) direction of the electronic device 300.

Referring to FIG. 3, the electronic device 300 according to one of certain embodiments may include a housing 310, a bezel 320, a display 340, an electronic component 350, a main circuit board 360, a bracket 380, a battery, and a biometric sensor 370. The structure of the housing 310 and/or the bezel 320 of the electronic device 300 illustrated in FIG. 3 may be identical to the structure of the housing 210, and/or the bezel 220 illustrated in FIG. 2A and FIG. 2B.

According to certain embodiments, the housing 310 may house and/or support various electronic components such as the display 340, the main circuit board 360, the electronic component 350, and/or the biometric sensor 370. A part of the housing 310, for example, the side surface of the housing 310 may be at least partially formed of a material that transmits radio signals or magnetic fields.

According to certain embodiments, the display 340 may be coupled to the transparent plate (for example, 211 in FIG. 2A) in the second direction (-Z-axis direction). The display 340 may display image information (for example, photographs and moving images) outwards through the transparent plate (for example, 211 in FIG. 2A) and may output screens for executing various applications (for example, gaming, Internet banking, and scheduling) according to the user's manipulation.

According to certain embodiments, the display 340 may include an LCD display, an LED display, an OLED display, a microelectromechanical system (MEMS) display, or an electronic paper display. The display 340 may have a touch screen panel integrated therewith such that the same can perform a touch screen function. According to certain embodiments, the display 340 may have an antenna radiator mounted on the inner or outer surface thereof such that the same can perform a wireless communication function.

According to certain embodiments, the display 340 may be electrically connected to a display circuit board 341, and the display circuit board 341 may be arranged inside the housing 310. The display circuit board 341 may deliver electric signals for driving the display 340.

According to certain embodiments, the main circuit board 360 may arranged to face the battery (not illustrated). The main circuit board 360 may have a processor, a communication module, and the like mounted thereon in integrated circuit types. The main circuit board 360 may be electrically connected to the battery. According to certain embodiments, the main circuit board 360 may be electrically connected to the electronic component 350, including an antenna radiator and the like, through a connector.

According to certain embodiments, the electronic component 350 is arranged on the main circuit board 360 and may include an antenna radiator and/or a wireless changing antenna. According to an embodiment, the antenna radiator may transmit/receive radio signals in a magnetic secure transmission (MST) type. For example, the antenna radiator may be an MST antenna. As another example, the antenna radiator may be a near-field communication (NFC) antenna transmitting/receiving radio signals in an NFC type. According to an embodiment, a shield structure may be arranged around the antenna radiator so as to block signal interference between the same and another electronic component (for example, sensor module).

According to certain embodiments, the wireless charging antenna may be attached to a surface of the main circuit board 360. The wireless charging antenna may be configured as a flat plate-type coil. The wireless charging antenna may be made of a conductive material and electrically connected to the main circuit board 360. The wireless charging antenna may generate an electric current by means of electromagnetic induction caused by an external electronic device. The electric current generated by the wireless charging antenna may charge the battery (not illustrated) through the main circuit board 360.

According to certain embodiments, a heat-radiating structure (not illustrated) may be provided between the main circuit board 360 and the battery. For example, the heat-radiating structure may receive heat generated by the main circuit board 360 so as to prevent the main circuit board 360 from being overheated.

According to certain embodiments, a shield structure 390 may be arranged between the main circuit board 360 and the second surface 315. The shield structure 390 may shield the space between the electronic component on the main circuit board 360 and the biometric sensor 370, thereby preventing interference between the same.

According to certain embodiments, the second surface 315 formed on the housing 310 in the second direction (-Z-axis direction) may form a rear cover of the housing 310. The rear cover may be made of a glass material. The rear cover may contact a part of the user's body (for example, wrist). According to certain embodiments, the material of the rear cover is not limited to glass, and the same may also be made of a transparent material such as transparent reinforced plastic. The center area of the rear cover may be made of a transparent plate for sensing operation of the biometric sensor 370, and the other area thereof may be made of an opaque plate. The rear cover may include at least one transparent area 315a such that light generated by the inner optical element is discharged outwards.

According to certain embodiments, the biometric sensor 370 may be arranged between the main circuit board 360 and the second surface 315 so as to sense the user's biometric information. For example, the biometric sensor 370 may include a heart rate monitoring (HRM) device. The biometric sensor 370 may sense blood vessel contraction/expansion caused by reflection of light resulting from a change in the amount of blood inside a blood vessel inside the skin of the user's body. The processor (for example, processor 120 in FIG. 1) may receive electric signals from the biometric sensor 370 and accordingly calculate the heart rate.

The biometric sensor 370 will be described later in more detail.

Figure 4:
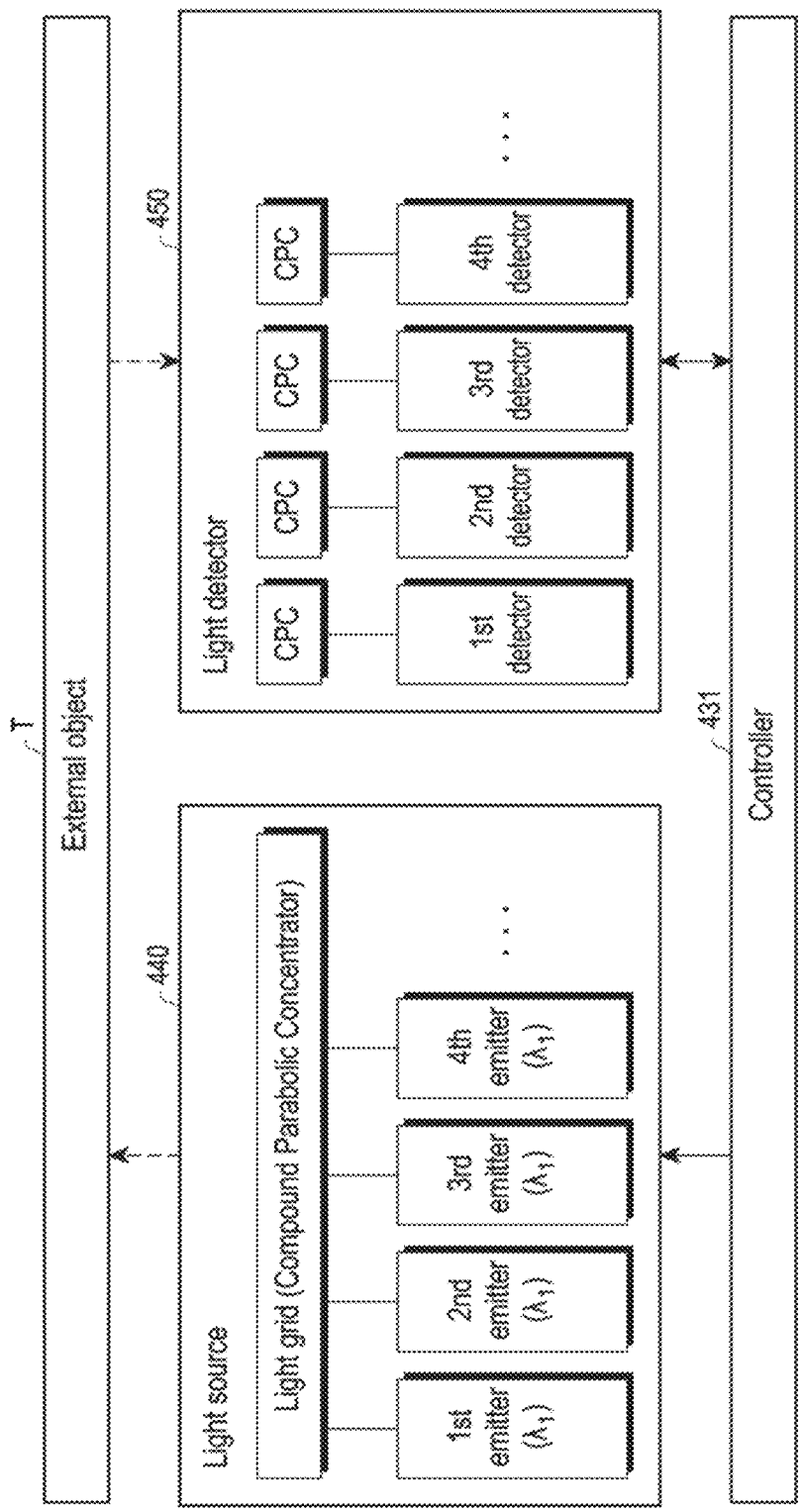
FIG. 4 is a block diagram illustrating the correlation between a biometric sensor module inside an electronic device according to certain embodiments and a user's body.

FIG. 4 is a block diagram illustrating the correlation between a biometric sensor module inside an electronic device according to certain embodiments and a user's body.

Referring to FIG. 4, the biometric sensor module inside an electronic device may include a light source (emitter) 440, a light detector (or sensor) 450, and a controller 431 configured to control the same.

According to certain embodiments, the biometric sensor 370 in FIG. 3 may be configured as a module which is connected to the controller 431 and/or the processor (for example, 120 in FIG. 1) or that which includes at least some of these constituent elements.

According to certain embodiments, the controller 431 may control operations of the light source 440 and the light detector 450 by providing electric signals thereto, and may receive signals received by the light detector 450. The controller 431 may be connected to the processor (for example, 120 in FIG. 1) so as to control the intensity of the light source 440, the driving channel, the driving period, and the like.

According to certain embodiments, one or both of the light source 440 and the light detector 450 may include a light guide (for example, compound parabolic collector "CPC" structure). The light guide may be arranged on the path of light generated by the light source 440 or light incident onto the light detector 450 so as to utilize each light and to guide the light such that the same can interact with a human tissue in a broken arrow type (using, for example, directional filtering).

According to certain embodiments, the light source 440 may be configured as a structure such that the same light may emit one wavelength or at least two wavelengths. The light source 440 may include at least one light emitting diode (LED) or a laser diode (LD), and each LED or LD may be configured to have a different wavelength. As another example, the light source 440 may include an array of multiple LEDs having the same wavelength.

According to certain embodiments, at least one light detector 450 may be formed so as to receive light which is emitted by the light source 440 and then reflected by a target (for example, the user's body). For example, the light detector 450 may sense light reflected or transmitted by a blood vessel inside skin. As another example, the light detector 450 may determine the presence of a target or may obtain an image of the shape of the target. The light detector may include a photodiode or an image sensor.

According to certain embodiments, the processor (for example, 120 in FIG. 1) may control the sensor module including the light source 440 and the light detector 450. For example, in the case of a sensor having multiple LEDs, it is possible to select an LED that is activated according to the biometric measurement type or the service. As another example, a green LED may be used to measure the heart rate and a red/IR LED may be activated to measure oxygen saturation (SpO2). As another example, according to skin color, the intensity of an LED may be adjusted, or the gain of the light detector may be controlled. As another example, the measurement period may be adjusted according to the service (for example, once in every minute or once in every hour), and the detailed operation may be controlled (for example, whether to monitor for 10 seconds or 20 seconds in a single measurement session). Such an operation may vary depending on the size of the battery of the electronic device, the power efficiency thereof, the amount of electricity consumed by the sensor, the purpose of use thereof, and the type thereof.

Figure 5:
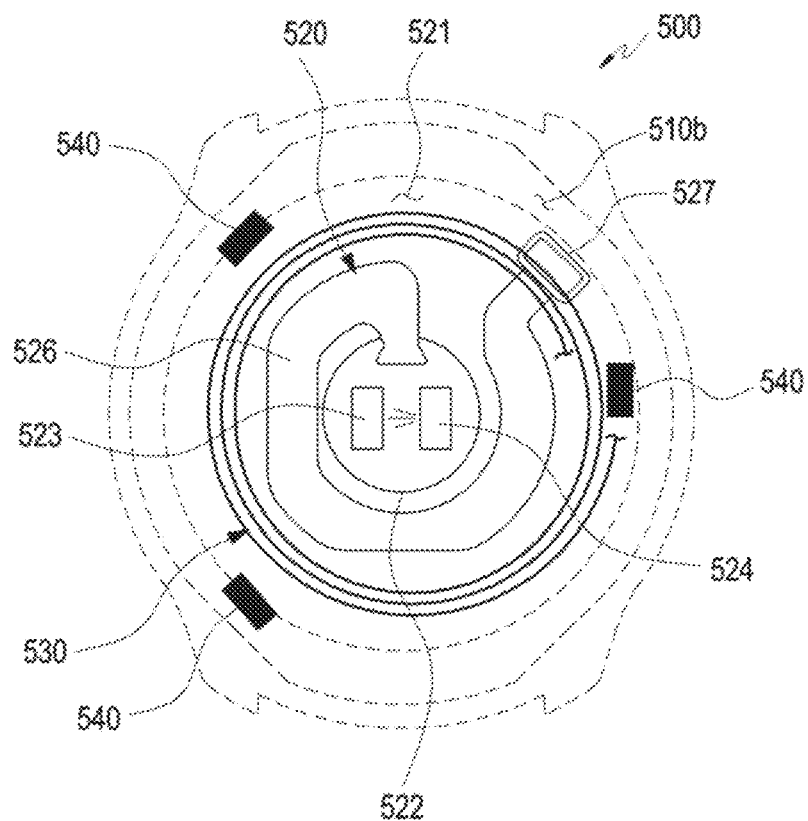
FIG. 5 is a conceptual diagram illustrating an electronic device including a biometric sensor, a wireless charging module, and a magnetic substance according to some embodiments.

FIG. 5 is a conceptual diagram illustrating an example electronic device 500 including a biometric sensor, a wireless charging module, and a magnetic substance according to some embodiments.

According to certain embodiments, the housing 510 (for example, 210 in FIG. 2) of the electronic device 500 may include a front plate and a rear plate 510*b*. The front plate may form a first surface (for example, 213 in FIG. 2) facing in the first direction, and the rear plate 510*b* may include a second surface (for example, 215 in FIG. 2) facing in the second direction that is opposite to the first direction. The second surface (for example, 215 in FIG. 2) of the rear plate 510*b* may include at least one substantially transparent area (for example, 215*a* in FIG. 2) such that light generated by an optical element (for example, light source) arranged inside the housing is emitted outwards.

The electronic device 500 may have various components, such as a biometric sensor module 520, a battery charging module 530 (for example, the wireless charging antenna included in the electronic component 350 in FIG. 3), and a magnetic substance 540, mounted adjacent to the second surface 521 (for example, 215 in FIG. 2) of the rear plate 510*b*. The biometric sensor module 520 may acquire the user's biometric information through the substantially transparent area (for example, 215*a* in FIG. 2) on the second surface 521 of the rear plate 510*b*.

Referring to FIG. 5, the biometric sensor module 520 may be arranged at the center portion on the second surface 521 of the rear plate 510*b*, and the battery charging module 530 and the magnetic substance 540 may be arranged around the biometric sensor module 520.

The biometric sensor module 520 may include a substrate 522 and may include a light source 523 and a light detector 524 inside the substrate 522. A circuit structure 526 may be connected to one side of the substrate 522, and the circuit structure 526 may extend to the edge of the second surface 521 to be connected to another electronic component (for example, power supply and/or processor) through a connector 527.

The wireless charging module 530 may be configured as a flat plate-type coil, and may generate an electric current by means of electromagnetic induction caused by an external electronic device (for example, wireless charging pad). The electronic device 500 may use the electric current generated by the wireless charging antenna so as to charge the battery (not illustrated) embedded in the electronic device 500. At least one magnetic substance 540 may be arranged on the peripheral portion of the battery charging module 530. The at least one magnetic substance 540 may be used to improve the cradling stability of the electronic device 500 and to guarantee that the battery charging operation of the device proceeds stably during charging.

According to some embodiments, as illustrated in FIG. 5, the biometric sensor module 520, the battery charging module 530, and the magnetic substance 540 may be arranged successively from the center portion of the second surface 521 of the rear plate 510*b*. In order to improve the cradling stability, three magnetic bodies 540 may be arranged radially as illustrated in FIG. 5.

According to some embodiments, it is when the battery charging module 530 and the magnetic substance 540 are positioned as close to the second surface 521 of the rear plate 510*b* as possible that the maximum efficiency of each constituent element can be obtained. Since the accuracy of the biometric sensor module 520 is increased when the same is positioned as close to a part of the user's body (for example, wrist) as possible, all of the biometric sensor module 520, the battery charging module 530, and the magnetic substance 540 may be substantially arranged adjacent to the second surface 521 of the rear plate 510*b*. This may limit, with regard to each of the biometric sensor module 520, the battery charging module 530, and the magnetic substance 540, the mutual component mounting characteristics and the design. For example, when mounting a coil included in the battery charging module 530, multiple magnetic bodies 540, if arranged on the peripheral portion thereof, may cause a design-related structural limitation, and the magnetic influence of the magnetic bodies 540 may affect the battery charging efficiency.

Hereinafter, there may be provided a wearable electronic device including a biometric sensor based on optics, which can improve component mounting characteristics and design degree-of-freedom, with reference to FIG. 6 to FIG. 12.

Figure 6:
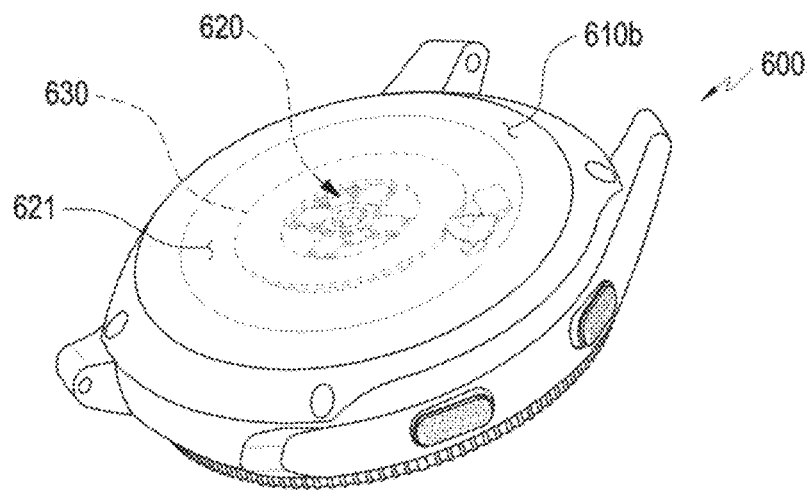
FIG. 6 is a perspective view illustrating the lower surface of an electronic device according to certain embodiments.

FIG. 6 is a perspective view illustrating the lower surface (for example, second surface) of an electronic device 600 according to certain embodiments.

Referring to FIG. 6, the electronic device 600 according to certain embodiments may include a biometric sensor module 620 and a wireless charging module 630 arranged adjacent to the second surface 621 of the rear plate 610*b*. The biometric sensor module 620 may be arranged at the center portion of the second surface 621, and the wireless charging module 630 may be around to surround the periphery of the biometric sensor module 620. According to an embodiment, at least a part (for example, circuit structure (for example, 526 in FIG. 5)) of the biometric sensor module 620 and at least a part (for example, flat plate-type coil mounting portion) of the wireless charging module 630 may overlap each other.

According to certain embodiments, the biometric sensor module 620 may be arranged in a space formed by the front plate and the rear plate 610*b*, as a specific example, between the main circuit board (for example, 360 in FIG. 3) and the second surface 621, so as to sense the user's biometric information.

The biometric sensor module 620 may be, for example, a sensor configured to collect or measure at least one biometric signal from the user. The biometric sensor module 620 may collect raw data for measuring at least one of the user's blood pressure, blood flow, heart rate number (HRM or HRV), body temperature, number of breaths, oxygen saturation (SpO2), cardiopulmonary sound detection, blood glucose, waist circumference, height, weight, body fat, amount of calories consumed, brainwaves, voice, skin resistance, electromyogram, electrocardiogram, gait, ultrasonic images, sleeping state, facial expression, pupil dilation, or blinking.

According to an embodiment, the electronic device 600 may analyze the biometric signal so as to generate biometric information (also referred to as biometric characteristic information). For example, a pulse-wave signal acquired through a heart rate variability (HRV) or heart rate monitor (HRM) sensor may be the biometric signal. The electronic device 600 may analyze the biometric signal so as to obtain primary biometric information such as the average number of heartbeats or heartbeat distribution and may process such biometric information so as to obtain secondary biometric information, such as higher-dimensional stress state or the degree of blood vessel aging.

According to an embodiment, the biometric sensor module 620 may simply output collected user biometric signals, or the biometric sensor module 620 may analyze biometric signals through the embedded processor and thus output biometric information. Therefore, biometric signals collected through the biometric sensor module 620 may be delivered to the processor inside the biometric sensor module 620, the processor (for example, 120 in FIG. 1) of the electronic device 600 in which the biometric sensor module is embedded, or a processor of an external device (for example, the server 106 or the electronic device 104 in FIG. 1) and used to produce biometric information.

When the electronic device 600 having the biometric sensor module 620 embedded therein has transmitted a biometric signal to a remote device (for example, the electronic device 104 in FIG. 1) or to the server (for example, the server 106 in FIG. 1) through a wired network, a wireless network, or direct connection, the remote device or the server, which has received the biometric signal, may process the biometric signal so as to generate biometric information. According to an embodiment, when the electronic device 600 having the biometric sensor module 620 embedded therein generates primary biometric information and transmits the generated biometric information to the remote device or the server, secondary biometric information may be generated by the remote device or the server.

For example, a biometric signal collected by the HRM sensor or the HRV sensor embedded in the electronic device 600 (for example, wrist watch) may be delivered to a smartphone (an example of a host or a main electronic device) wirelessly connected to the electronic device 600, and the smartphone may analyze the received biometric signal and generate biometric information. The biometric information may be transmitted through a wired or wireless communication means such that the same can be displayed by the display of the smartphone or by the display of the wrist watch device. For example, at least one of the smartphone or the wrist watch device can display or store the biometric information. According to an embodiment, a biometric signal collected by an HRM sensor or HRV sensor having an embedded ear clip having an earphone function may be delivered to the wrist watch device or the smartphone, and the electronic device 600 or the smartphone may generate biometric information. The generated biometric information may be delivered to at least one different device. If the smartphone has generated biometric information, the electronic device 600 that has received the biometric information may display the same through the display (for example, 340 in FIG. 3), and the ear clip that has received the biometric information may provide the same to the user through a sound.

According to an embodiment, a heart rate sensor may be used as the biometric sensor module 620. For example, the amount of blood flow in a peripheral blood vessel changes as the heart repeatedly contracts and dilates, and the volume of the blood vessel changes accordingly. A photoplethysmography (PPG) sensor, which is a type of heart rate sensor, measures the amount of transmitted light by using a photosensor and shows the waveform of the heartbeat. This technology can be used to measure a change in the amount of blood in the blood vessel or the oxygen saturation (SpO2). The heart rate sensor may be embedded in a clip, a wrist watch, a necklace, a band, or a cellphone, and a biometric signal may be measured by attaching the heart rate sensor to a body part (for example, ear, wrist, carotid artery, finger, or ankle) or by bringing the same into contact therewith. For example, when a measurement is made through a finger, a heart rate sensor including a light source and a light detector is brought into contact with a finger, and the contact is maintained for at least a predetermined period of time. Then, an increased amount of blood flows through the finger during a systole, thereby reducing the amount of light passing through the finger, and a decreased amount of blood flows during a diastole, thereby increasing the amount of light passing the finger. Such a change is used to measure a biometric signal.

The biometric sensor module 620 (for example, heart rate sensor) may detect the amount of transmission through the finger in terms of a voltage. In addition, the biometric sensor module 620 (for example, heart rate sensor) or the electronic device 600 may convert the detected voltage into a digital value, thereby measuring the frequency of the change. Based on the detected voltage, the biometric sensor module 620 (for example, heart rate sensor) or the electronic device 600 may determine how may pulses occur per second, and this may be used to calculate the number of heartbeats or the duration between heartbeats. When the electronic device (for example, 600) has a PPG sensor embedded therein as a heart rate sensor, a biometric signal may be detected through the radial artery or through the ulnar artery, and it is possible to measure a biometric signal through locations at which blood vessels are distributed, which are not necessarily the above-mentioned arteries. In addition, since there is a delay time between occurrence of a signal at the heart and delivery thereof to each part of the body, there may be a time difference between an electrocardiogram signal and a heartbeat signal. For example, when a heart rate sensor is mounted on a wrist watch device or an ear clip, there may be a time delay when a signal is delivered from the heart to the wrist or ear. The number of heartbeats per minute differs depending on the age of the subject, and the heartbeat pattern may vary depending on health status and emotional status. The electronic device 600 may measure the degree of elasticity of the blood vessel through pulse wave analysis and may determine the degree of aging of the blood vessel based on the same. That is, through analysis of accelerated plethysmo (APG) obtained by second-order differentiation of the pulse-wave signal, the electronic device may analyze the strength of cardiac output, blood vessel elasticity, and the amount of remaining blood. This enables automatic analysis of the blood circulation status, such as the degree of elasticity of the blood vessel or the hardness thereof and makes it possible to conduct auxiliary tests regarding high blood pressure, diabetes, hyperlipidemia, arteriosclerosis, heart disease, and peripheral circulatory disturbance.

In the embodiment illustrated in FIG. 6, the magnetic substance (for example, 640 in FIG. 7 described later) may be integrated with the biometric sensor module 620, unlike the embodiment illustrated in FIG. 5.

Figure 7:
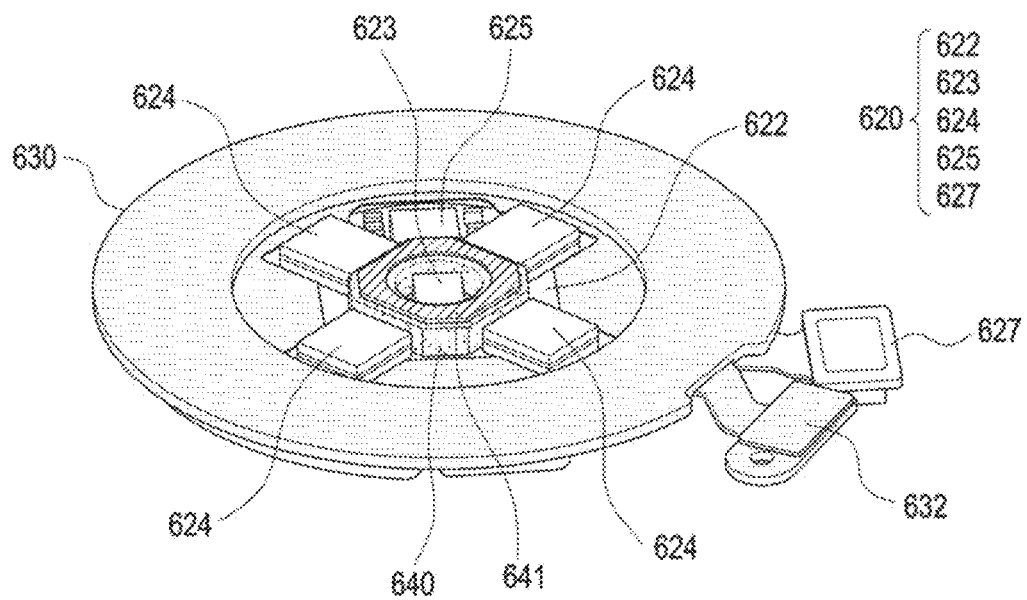
FIG. 7 is a perspective view illustrating a biometric sensor module, a wireless charging module, and a magnetic substance according to certain embodiments.

FIG. 7 is a perspective view illustrating a biometric sensor module (for example, 620 in FIG. 6), a wireless charging module 630, and a magnetic substance 640 according to certain embodiments.

Referring to FIG. 7, the biometric sensor module (for example, 620 in FIG. 6) may include a substrate 622, at least one light source 623 arranged between the substrate 622 and the rear plate (for example, 610*b* in FIG. 6) so as to emit light outwards, and at least one light detector 624 configured to receive reflected light corresponding to the light emitted from the light source 623.

According to certain embodiments, the at least one light source 623 may be mounted on the substrate 622 so as to transmit light in the second direction (for example, −Z-axis direction in FIG. 3). The at least one light source 623 may emit light toward an external object (for example, the user's body), and the at least one light detector 624 may receive light reflected at the external object. According to an embodiment, the at least one light source 623 and the at least one light detector 624 may be arranged on the same plane. For example, the light detector 624 may be arranged on a surface (for example, a surface facing in the second direction (−Z-axis direction)) of the substrate 622 and electrically connected to the substrate 622, and the light source 623 may be arranged thereon at a predetermined distance from the light source 624. The light source 623 may also be arranged on the surface of the substrate 622 and electrically connected to the substrate 622.

The biometric sensor module (for example, 620 in FIG. 6) may further include a biometric sensor driver 625. For example, the biometric sensor driver 625 may be arranged on a surface (for example, a surface facing in the second direction (−Z-axis direction)) of the substrate 622 and electrically connected to the substrate 622.

According to an embodiment, it may be efficient for the light detector 624 to have a large area, in order to receive reflected light sufficiently. Therefore, the area of the light detector 624 may be larger than that of the light source 623.

According to certain embodiments, the biometric sensor module 620 may further include a magnetic substance 640. The magnetic substance 640 is configured to correspond to a magnetic substance (not illustrated) provided on an external electronic device (for example, wireless charging pad (not illustrated)) so as to improve the cradling stability of the electronic device (for example, 600 in FIG. 6) and to guarantee that the antenna provided on the wireless charging pad and the wireless charging module 630 are aligned with each other, thereby ensuring a stable charging operation.

According to certain embodiments, the magnetic substance 640 may be used as a wall structure. By using the magnetic substance 640 as a wall structure, it is possible to block the direct path, along which the light emitted by the light source 623 is received by the light detector 624 without being transmitted out of the electronic device 600, thereby preventing interference of light other than the reflected light from reaching the light detector 624.

The magnetic substance 640 may be shaped to surround the periphery of the light source 623. According to an embodiment, the magnetic substance 640 may have the shape of an octagonal column having a cylindrical recess R therein, as illustrated in FIG. 7. However, the shape is not limited thereto, and various other shapes may also be adopted depending on the type, number, and arrangement of neighboring electronic components. The magnetic substance 640 may also be arranged on the substrate 622 as in the case of the light source.

According to certain embodiments, the biometric sensor module 620 may further include a member 641. Accordingly, the magnetic substance 640 and the member 641 may form a stacking structure. According to an embodiment, the member 641 may be positioned on the upper surface of the magnetic substance 640 and may include an adhesive material and/or a shock-absorbing material. The adhesive material may include, for example, a material that can be attached in a bonding type, in a tape type, or in a double-sided tape type. The shock-absorbing material may include, for example, sponge or rubber.

According to an embodiment, the member 641, arranged between the light source 623 and the light detector 624, may also include a light-blocking material in order to prevent light leaking.

Figure 8:
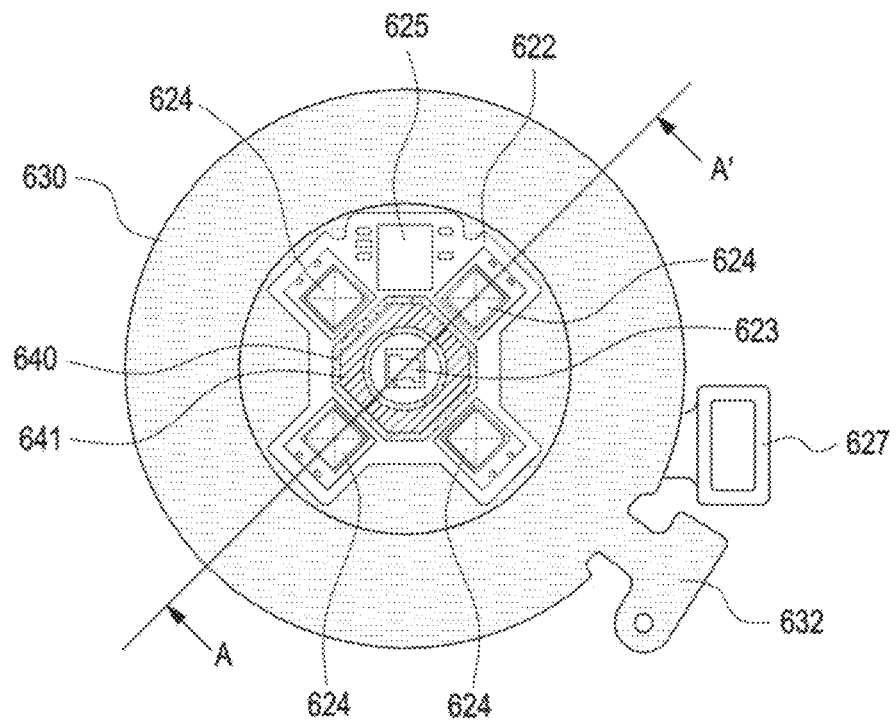
FIG. 8 is a front view illustrating a biometric sensor module, a wireless charging module, and a magnetic substance according to certain embodiments.

FIG. 8 is a front view illustrating a biometric sensor module (for example, 620 in FIG. 6), a wireless charging module 630, and a magnetic substance 640 according to certain embodiments.

According to the embodiment illustrated in FIG. 7 and FIG. 8, one light source 623 may be arranged in the center area of the substrate 622, and four light detectors 624 may be radially arranged on the same substrate 622 on which the light source 623 is arranged at a predetermined distance from the light source 623. It is to be noted that, although four light detectors 624 are illustrated in FIG. 7, the number of light detectors 624 and the angle between the same may vary in certain embodiments.

The embodiment in FIG. 7 and FIG. 8 may illustrate the circuit structure (for example, 526) illustrated in FIG. 5, which is hidden by the wireless charging module 630. The circuit structure extending from one side of the substrate 622 to the outside of the biometric sensor module (for example, 620 in FIG. 6) may have a biometric sensor connector 627 formed on an end thereof and may be connected to electronic components (for example, 350 in FIG. 3) arranged on the main circuit board (for example, 360 in FIG. 3).

The wireless charging module 630 may have a flat-type wireless charging coil (not illustrated) formed therein. A connector 632 may be provided on one side of the wireless charging module and connected to the wireless charging coil such that power can be supplied from the outside.

According to certain embodiments, the wireless charging module 630 may play the role of surrounding the biometric sensor module (for example, 620 in FIG. 6) and shielding the periphery of the biometric sensor module. As in the embodiment illustrated in FIG. 7 and FIG. 8, the wireless charging module 630 may be formed so as to surround the peripheries of the light detectors 624 that slightly protrude outwards from the biometric sensor module (for example, 620 in FIG. 6).

Figure 9:
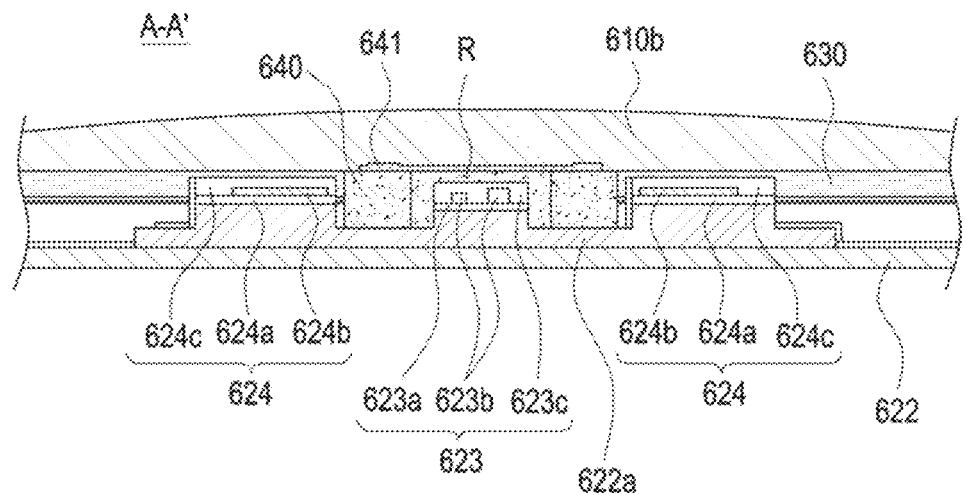
FIG. 9 is a sectional view illustrating a biometric sensor module, a wireless charging module, and a magnetic substance according to certain embodiments.

FIG. 9 is a sectional view illustrating a biometric sensor module (for example, 620 in FIG. 6), a wireless charging module 630, and a magnetic substance 640 according to certain embodiments. FIG. 9 may illustrate a section of the embodiment illustrated in FIG. 8 taken along A-A'.

According to an embodiment, the substrate 622 may independently play the role of a bracket, or may further include a bracket on a surface thereof. FIG. 9 illustrates a separate bracket 622*a* provided on the substrate 622. According to an embodiment, the bracket 622*a* may be integrated with the substrate 622. The light source 623 and the light detector 624, when seated on the bracket 622*a*, may be positioned close to the second surface 621 of the rear plate 610b while having a predetermined height from the base of the substrate 622.

According to certain embodiments, the light source 623 may include an LED, and the light detector 624 may include a photodiode. The light source 623 may emit light in various color ranges. The emitted light may have a wavelength range from about 380 nm to 800 nm. As another example, the light source 623 may emit green light having a wavelength range from about 492 nm to 575 nm.

In order to protect the element 623b emitting light on the inner circuit board 623a, the light source 623 may include a capping portion 623c that caps the peripheral portion of the inner circuit board 623a and that of the element 623b. The capping portion 623c may be made of epoxy, for example.

According to an embodiment, in order to protect the element 624b emitting light on the inner circuit board 624a, the light detector 624 may include a capping portion 624c that caps the peripheral portion of the inner circuit board 624a and that of the element 624b. The capping portion 624c may be made of epoxy, for example.

Referring to FIG. 9, a magnetic substance 640 is arranged between the light source 623 and the light detector 624 so as to play the role of a wall structure. The magnetic substance 640 may prevent the other part of the light emitted by the light source 623 than the reflected light from reaching the light detector 624. To this end, the stacking structure of the magnetic substance 640 and the member 641 may have a height at least equal to or larger than the height of the light source 623 and that of the light detector 624.

A recess R is formed inside the stacking structure of the magnetic substance 640 and the member 641, which has a wall structure shape. The electronic device (for example, 600 in FIG. 6) according to an embodiment may acquire biometric information in the following procedure: Light emitted by the light source 623, while the light source 623 is arranged in the recess R, passes through the substantially transparent portion (for example, 315a in FIG. 3) of the rear plate 610b and reaches an external object. A part of the light is reflected at the external object and is incident back onto the light detector 624.

According to an embodiment, the light source 623 and the light detector 624 may further include a light guide on the light movement path, although not illustrated separately, so as to improve the straightforwardness in the light traveling direction and to reduce the influence of noise.

According to the embodiments illustrated in FIG. 6 to FIG. 9, the electronic device including a biometric sensor module 620, a wireless charging module 630, and a magnetic substance 640 arranged adjacent to the second surface 621 of the rear plate 610b is advantageous in that, since the magnetic substance 640 is arranged inside the wireless charging module 630 together with the biometric sensor module 620, limitations on the design of the wireless charging module 630 can be reduced. In addition, since the magnetic substance 640 can be used as a wall structure of the biometric sensor module 620, it is possible to prevent light emitted by the light source 623 from reaching the light detector 624, except for reflected light, and to make the electronic device more compact.

Figure 10:
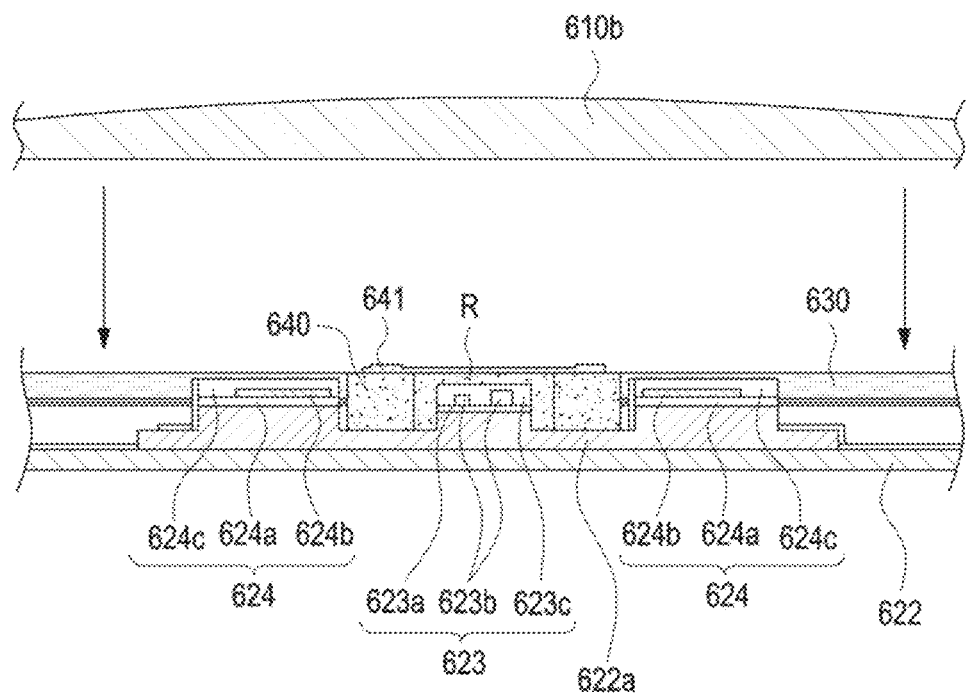
FIG. 10 is a sectional view illustrating a method for assembling a biometric sensor module, a wireless charging module, and a magnetic substance according to an embodiment.

FIG. 10 is a sectional view illustrating a method for assembling a biometric sensor module 620, a wireless charging module 630, and a magnetic substance 640 according to an embodiment.

As described above, the electronic device (for example, 600 in FIG. 6) may have such a structure that a biometric sensor module 620 is mounted on a substrate 622, and the biometric sensor module 620 and a wireless charging module 630 are stacked and arranged. In addition, a rear plate 610b may be configured to cover the upper surface of the biometric sensor module 620 and that of the wireless charging module 630.

According to an embodiment, after the rear plate 610b covers the upper surface of the biometric sensor module 620 and that of the wireless charging module 630, and is then forced against the same, the rear plate 610b and the biometric sensor module 620 may be bonded and fixed to each other by a member 641 including an adhesive material. According to an embodiment, if the member 641 further includes a light-blocking material, light emitted by the light source 623 may be substantially blocked, except for the light movement path through the rear plate 610b.

According to an embodiment, the magnetic substance 640 may be forced against the rear plate 610b while being already assembled to the biometric sensor module 620. For example, the magnetic substance 640 may have a member 641 formed on the upper surface (for example, surface facing in a direction parallel to the −Z-axis in FIGS. 3) and may be fixed to the substrate 622 or the bracket 622a by means of a bonding member (not illustrated) formed on the back surface (for example, surface facing in a direction parallel to the +Z-axis in FIG. 3) of the magnetic substance 640. Alternatively, the magnetic substance 640 may be implemented as a part of the biometric sensor module 620 while being fixed to the substrate 622 or the bracket 622a by a fasting member (not illustrated) provided on the back surface of the magnetic substance 640.

Figure 11:
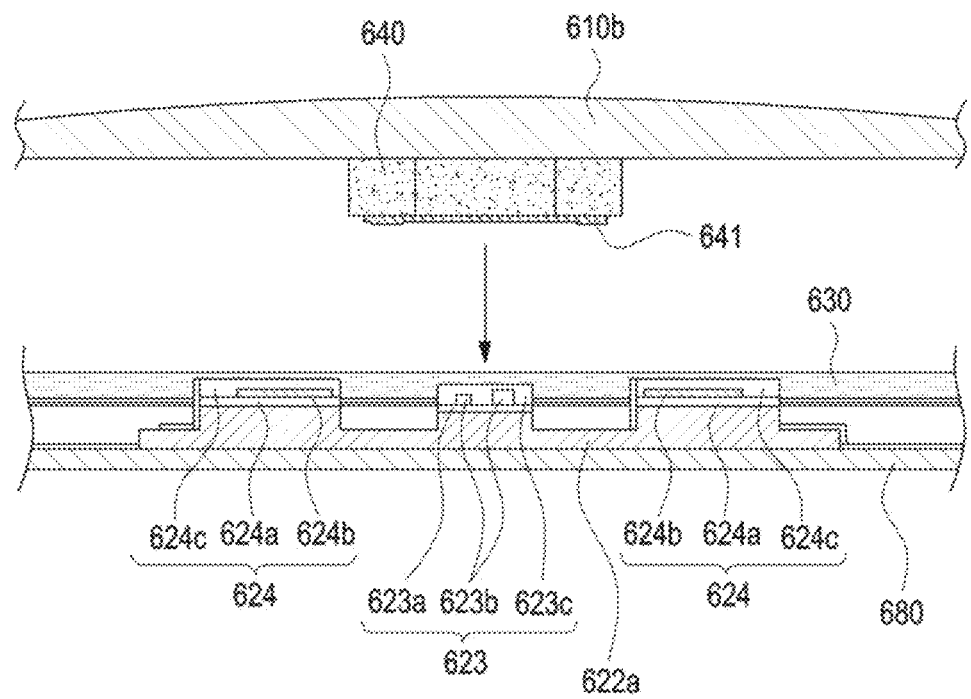
FIG. 11 is a sectional view illustrating a method for assembling a biometric sensor module, a wireless charging module, and a magnetic substance according to another embodiment.

FIG. 11 is a sectional view illustrating a method for assembling a biometric sensor module 620, a wireless charging module 630, and a magnetic substance 640 according to another embodiment.

As described above, the electronic device (for example, 600 in FIG. 6) may have such a structure that a biometric sensor module 620 is mounted on a substrate 622, and the biometric sensor module 620 and a wireless charging module 630 are stacked and arranged. In addition, a rear plate 610b may be configured to cover the upper surface of the biometric sensor module 620 and that of the wireless charging module 630.

Unlike the embodiment illustrated in FIG. 10, according to the embodiment illustrated in FIG. 11, the magnetic substance 640, which is already assembled to the rear plate 610b, may be coupled to the biometric sensor module 620 by coupling the rear plate 610b to the biometric sensor module 620. For example, the magnetic substance 640 may have a member 641 formed on the back surface thereof (for example, surface facing in a direction parallel to the +Z-axis in FIG. 3) and may be fixed to the substrate 622 or the bracket 622a by means of a bonding member (not illustrated) formed on the upper surface of the magnetic substance 640. Alternatively, the magnetic substance 640 may remain fixed to the rear plate 610b by means of a fastening member (not illustrated) provided on the upper surface thereof (for example, surface facing in a direction parallel to the −Z-axis in FIG. 3). According to the embodiment illustrated in FIG. 11, it is when the rear plate 610b is coupled to the biometric sensor module 620 that the magnetic substance 640 implements a part of the biometric sensor module 620.

Figure 12:
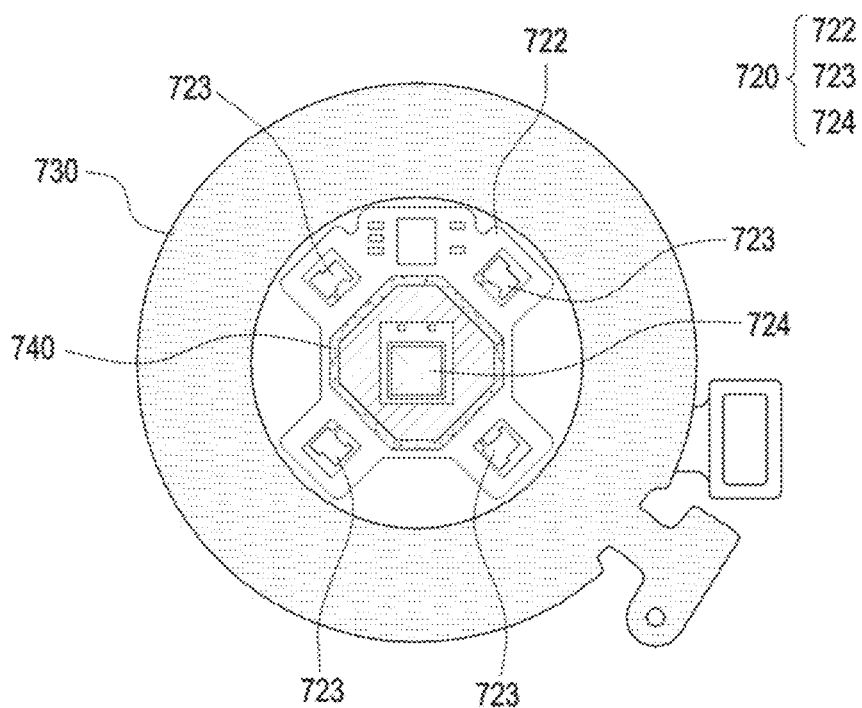
FIG. 12 is a front view illustrating a biometric sensor module, a wireless charging module, and a magnetic substance according to another embodiment.

FIG. 12 is a front view illustrating a biometric sensor module 720, a wireless charging module 730, and a magnetic substance 740 according to another embodiment.

Referring to FIG. 12, the electronic device (for example, 600 in FIG. 6) may include a biometric sensor module 720 and a wireless charging module 730 arranged adjacent to the second surface 721 of the rear plate 710b. The biometric sensor module 720 may be arranged at the center portion of the second surface (for example, 621 in FIG. 6), and the wireless charging module 730 may be arranged to surround the periphery of the biometric sensor module 720. According to an embodiment, at least a part (for example, circuit structure (for example, 526 in FIG. 5)) of the biometric sensor module 720 and at least a part (for example, flat plate-type coil mounting portion) of the wireless charging module 730 may overlap each other.

According to certain embodiments, the biometric sensor module 720 may be arranged in a space formed by the front plate and the rear plate 710b, as a specific example, between the main circuit board (for example, 360 in FIG. 3) and the second surface (for example, 621 in FIG. 6), so as to sense the user's biometric information.

The biometric sensor module 720 may include a substrate 722, at least one light source 723 arranged between the substrate 722 and the rear plate (for example, 610b in FIG. 6) so as to emit light outwards, and at least one light detector 724 configured to receive reflected light corresponding to the light emitted from the light source 723.

In the embodiment illustrated in FIG. 12, the at least one light source 723 may be mounted on the substrate 722 so as to transmit light in the second direction (for example, −Z-axis direction in FIG. 3). The at least one light source 723 may emit light toward an external object (for example, the user's body), and the at least one light detector 724 may receive light reflected at the external object. According to an embodiment, it may be efficient for the light detector 724 to have a large area, in order to receive reflected light sufficiently. Therefore, the area of the light detector 724 may be larger than that of the light source 723.

According to certain embodiments, the biometric sensor module 720 may further include a magnetic substance 740. The magnetic substance 740 may be shaped to surround the periphery of the light detector 724. According to an embodiment, four light sources 723 may be radially arranged outside the magnetic substance 740, and one light detector 724 may be surrounded by the magnetic substance 740. It is to be noted that, although four light sources 723 are illustrated in FIG. 12, the number of light sources 723 and the angle between the same may vary in certain embodiments.

Descriptions of the other elements of the embodiment illustrated in FIG. 12 than those described above are identical to those described with reference to FIG. 1 to FIG. 11, and thus will not be repeated herein.

An electronic device according to certain embodiments disclosed herein may be various types of devices. The electronic devices may include, for example, a portable communication device (e.g., a smartphone), a computer device, a portable multimedia device, a portable medical device, a camera, a wearable device, or a home appliance. According to an embodiment, the electronic devices are not limited to those described above.

It should be appreciated that certain embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. In this document, each of the expressions "A or B", "at least one of A and B", "at least one of A or B", "A, B, or C", "at least one of A, B, and C", and "at least one of A, B, or C" may include one of items enumerated together in the corresponding expression, among the expressions, or all possible combinations thereof. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," or "connected with,", it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the invoked at least one instruction. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more components of the above-described components or operations may be omitted, or one or more other components or operations may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

According to certain embodiments, there may be provided a wearable electronic device (for example, 600 in FIG. 6) including: a housing (for example, 610 in FIG. 6) including a front plate facing in a first direction (for example, direction parallel to the +Z-axis in FIG. 3), a rear plate (for example, 610b in FIG. 6) facing in a direction opposite to the first direction (for example, direction parallel to the −Z-axis in FIG. 3), at least a part of the rear plate being substantially transparent, and a side member forming a space between the front plate and the rear plate; a substrate (for example, 622 in FIG. 7) arranged in the space; a biometric sensor module (for example, 620 in FIG. 7) arranged between the substrate and the rear plate, the biometric sensor module including at least one light source (for example, 623 in FIG. 7) configured to emit light outwards and at least one light detector (for example, 624 in FIG. 7) configured to receive reflected light corresponding to the light emitted from the light source; and at least one magnetic substance (for example, 640 in FIG. 7) arranged between the light source and the light detector such that provision of light other than the reflected light to the light detector is limited.

According to certain embodiments, the magnetic substance may be arranged to surround the light source or the light detector.

According to certain embodiments, the biometric sensor module may further include: a biometric sensor driver (for example, 625 in FIG. 7); a bracket (for example, 622a in FIG. 9) on which the biometric sensor driver, the light source, and the light detector are seated; a circuit structure (for example, 526 in FIG. 5) extending from one side of the substrate or the bracket; and a biometric sensor connector (for example, 627 in FIG. 7) formed on an end of the circuit structure.

According to certain embodiments, the wearable electronic device may further include a member (for example, 641 in FIG. 7), and the magnetic substance and the member may form a stacking structure.

According to certain embodiments, the member may include an adhesive material.

According to certain embodiments, the member may include a shock-absorbing material.

According to certain embodiments, the stacking structure of the magnetic substance and the member may have a height formed to be equal to or larger than a height of the light source and a height of the light detector.

According to certain embodiments, the wearable electronic device may further include a wireless charging module.

According to certain embodiments, the wireless charging module may be arranged to surround at least a part of the optical biometric sensor module.

According to certain embodiments, the wearable electronic device may further include a wireless charging module, and the wireless charging module may be stacked and arranged on an upper surface of the circuit structure.

According to certain embodiments, the light source may be arranged, when seen from an upper surface of the rear plate, in a center area of the rear plate, the magnetic substance may be formed to surround a periphery of the light source, and multiple light detectors may be arranged radially around the magnetic substance.

According to certain embodiments, the light detector may be arranged, when seen from an upper surface of the rear plate, in a center area of the rear plate, the magnetic substance may be formed to surround a periphery of the light detector, and multiple light sources may be arranged radially around the magnetic substance.

According to certain embodiments, the magnetic substance may be seated on the substrate or the bracket, and the wearable electronic device may further include a member between the magnetic substance and the rear plate.

According to certain embodiments, the magnetic substance may be seated on the rear plate, and the wearable electronic device may further include a member between the magnetic substance and the substrate.

According to certain embodiments, the light source of the biometric sensor module may be configured to emit light to the rear plate, at least a part of which is substantially transparent, and the light detector may be configured to receive light which is emitted through the rear plate, and which is reflected by an external object, thereby acquiring biometric information of the external object.

According to certain embodiments, there may be provided a wearable electronic device (for example, 600 in FIG. 6) including: a housing (for example, 610 in FIG. 6) including a front plate facing in a first direction (for example, direction parallel to the −Z-axis in FIG. 3), a rear plate (for example, 610b in FIG. 6) facing in a direction opposite to the first direction (for example, direction parallel to the +Z-axis in FIG. 3), at least a part of the rear plate being substantially transparent, and a side member (for example, 610c in FIG. 6) forming a space between the front plate and the rear plate; a substrate (for example, 622 in FIG. 7) arranged in the space; an optical biometric sensor module (for example, 620 in FIG. 7) arranged between the substrate and the rear plate, the optical biometric sensor module including an optical biometric sensor driver (for example, 625 in FIG. 7), at least one light source (for example, 723 in FIG. 7) configured to emit light outwards, at least one light detector (for example, 624 in FIG. 7) configured to receive reflected light corresponding to the light emitted from the light source, a bracket (for example, 622a in FIG. 7) on which the optical biometric sensor driver, the light source, and the light detector are seated, a circuit structure (for example, 526 in FIG. 5) extending from one side of the substrate, and an optical biometric sensor connector (for example, 627 in FIG. 7) formed on an end of the circuit structure; a wireless charging module (for example, 630 in FIG. 7) configured to wirelessly charge the wearable electronic device; at least one magnetic substance (for example, 640 in FIG. 7) arranged between the light source and the light detector; and a member (for example, 641 in FIG. 7) forming a stacking structure with the magnetic substance, wherein the wireless charging module is arranged to surround at least a part of the optical biometric sensor module, and the magnetic substance has a wall formed thereon such that provision of light other than the reflected light to the light detector is limited.

It would be obvious to a person skilled in the art to which the disclosure pertains that the above-described electronic device according to certain embodiments is not limited to the above-mentioned embodiments and drawings, but could be variously substituted, changed, and modified within the technical disclosure.

What is claimed is:

1. A wearable electronic device, comprising:
    a housing comprising a front plate disposed facing in a first direction, a rear plate disposed facing in a second direction opposite to the first direction, at least a part of the rear plate substantially transparent, and a side member coupled to the front and rear plates to define a space between the front plate and the rear plate;
    a substrate disposed within the space;
    a biometric sensor module disposed between the substrate and the rear plate, the biometric sensor module including at least one light source configured to emit light to an exterior of the wearable electronic device and at least one light detector configured to receive the emitted light reflected from the exterior;
    at least one magnetic substance disposed between the light source and the light detector to limit an amount of light reaching the biometric sensor module other than the emitted light reflected from the exterior; and
    a member,
    wherein the magnetic substance includes a wall formed thereon to limit an incident of light reaching the light detector other than the reflected emitted light,
    wherein the magnetic substance and the member together form a stacking structure, and
    wherein the member includes a light-blocking material in order to prevent light leakage.

2. The wearable electronic device of claim 1, wherein the at least one magnetic substance at least partially surrounds at least one of the light source or the light detector.

3. The wearable electronic device of claim 1, wherein the biometric sensor module further comprises:
    a biometric sensor driver;
    a bracket on which the biometric sensor driver, the light source, and the light detector are seated;
    a circuit structure extending from one side of the substrate or the bracket; and
    a biometric sensor connector formed on an end of the circuit structure.

4. The wearable electronic device of claim 1, wherein the member comprises an adhesive material.

5. The wearable electronic device of claim 1, wherein the member comprises a shock-absorbing material.

6. The wearable electronic device of claim 1, wherein the stacking structure of the magnetic substance and the member includes a height equal to or larger than a height of the light source and a height of the light detector.

7. The wearable electronic device of claim 1, further comprising a wireless charging module.

8. The wearable electronic device of claim 7, wherein the wireless charging module is disposed as to surround at least a part of the biometric sensor module.

9. The wearable electronic device of claim 1, further comprising a wireless charging module, wherein the wireless charging module is disposed on an upper surface of the circuit structure.

10. The wearable electronic device of claim 1, wherein the light source is disposed in a central area of the rear plate, the magnetic substance is disposed to circumferentially surround at least part of the light source, and multiple light detectors are disposed radially around the magnetic substance.

11. The wearable electronic device of claim 1, wherein the light detector is disposed in a central area of the rear plate, the magnetic substance is disposed to circumferentially surround at least part of the light detector, and multiple light sources are disposed radially around the magnetic substance.

12. The wearable electronic device of claim 3, wherein the magnetic substance is seated on the substrate or the bracket, and the wearable electronic device includes a member disposed between the magnetic substance and the rear plate.

13. The wearable electronic device of claim 12, wherein the magnetic substance is seated on the rear plate, and wherein the wearable electronic device includes a member is disposed between the magnetic substance and the substrate.

14. The wearable electronic device of claim 1, wherein the light source is configured to emit light through the rear plate, at least a part of the rear plate being substantially transparent, and wherein the light detector is configured to receive light is emitted through the rear plate, and reflected by an external object, to acquire biometric information associated with the external object.

15. A wearable electronic device, comprising:
    a housing comprising a front plate disposed facing in a first direction, a rear plate disposed facing in a second direction opposite to the first direction, at least a part of the rear plate being substantially transparent, and a side member coupled to the front and rear plates to define a space between the front plate and the rear plate;
    a substrate disposed within the space;
    an optical biometric sensor module disposed between the substrate and the rear plate, the optical biometric sensor module, including:
        an optical biometric sensor driver, at least one light source configured to emit light to an exterior of the wearable electronic device,
        at least one light detector configured to receive the emitted light reflected from the exterior,
        a bracket on which the optical biometric sensor driver, the light source, and the light detector are seated,
        a circuit structure extending from one side of the substrate, and
        an optical biometric sensor connector formed on an end of the circuit structure;
    a wireless charging module configured to wirelessly charge the wearable electronic device;
    at least one magnetic substance configured to be arranged between the light source and the light detector; and
    a member configured to form a stacking structure together with the magnetic sub stance,
    wherein the wireless charging module is disposed so as to circumferentially surround at least a part of the optical biometric sensor module,
    wherein the magnetic substance includes a wall formed thereon to limit an incident of light reaching the light detector other than the reflected emitted light, and
    wherein the member include a light-blocking material in order to prevent light leakage.

16. The wearable electronic device of claim 15, wherein the light source is disposed in a central area of the rear plate, the at least one magnetic substance circumferentially surrounds at least part of the light source, and multiple light detectors are disposed radially around the magnetic substance.

17. The wearable electronic device of claim 15, wherein the light detector is disposed in a central area of the rear plate, the magnetic substance circumferentially surrounds at least part of a periphery of the light detector, and multiple light sources are disposed radially around the magnetic substance.

18. The wearable electronic device of claim 15, wherein the magnetic substance is seated on the substrate or the bracket, and wherein the wearable electronic device further includes a member disposed between the magnetic substance and the rear plate.

19. The wearable electronic device of claim 15, wherein the magnetic substance is seated on the rear plate, and wherein the wearable electronic device further comprises a member disposed between the magnetic substance and the substrate.

* * * * *